(12) United States Patent
Tralshawala et al.

(10) Patent No.: US 9,297,770 B2
(45) Date of Patent: Mar. 29, 2016

(54) SYSTEMS AND METHODS FOR NON-DESTRUCTIVELY MEASURING CALORIE CONTENTS OF FOOD ITEMS

(75) Inventors: Nilesh Tralshawala, Rexford, NY (US); John Frederick Graf, Ballston Lake, NY (US); Jack Mathew Webster, Colonie, NY (US); Vasile Bogdan Neculaes, Niskayuna, NY (US); Sarah Lillian Katz, Albany, NY (US)

(73) Assignee: General Electric Company, Schenectady, NY (US)

( * ) Notice: Subject to any disclaimer, the term of this patent is extended or adjusted under 35 U.S.C. 154(b) by 1278 days.

(21) Appl. No.: 13/193,887

(22) Filed: Jul. 29, 2011

(65) Prior Publication Data

US 2013/0027060 A1    Jan. 31, 2013

(51) Int. Cl.
*G01K 17/20* (2006.01)
*G01N 22/04* (2006.01)
*G01N 33/02* (2006.01)

(52) U.S. Cl.
CPC ............... *G01N 22/04* (2013.01); *G01N 33/02* (2013.01)

(58) Field of Classification Search
USPC ......................................... 177/25.16; 219/518
See application file for complete search history.

(56) References Cited

U.S. PATENT DOCUMENTS

| | | | |
|---|---|---|---|
| 5,254,819 A * | 10/1993 | Yoshino | H05B 6/6467 219/709 |
| 6,987,393 B2 | 1/2006 | Jean et al. | |
| 7,804,456 B2 * | 9/2010 | Yekeh Yazdandoost | H01Q 1/38 343/741 |
| 2005/0169388 A1 * | 8/2005 | Toland | H04B 1/71635 375/259 |
| 2007/0218174 A1 | 9/2007 | Hanamatsu et al. | |
| 2009/0281414 A1 * | 11/2009 | Feldman | A61B 5/04005 600/409 |
| 2010/0187224 A1 * | 7/2010 | Hyde | H05B 6/705 219/720 |

OTHER PUBLICATIONS

Lanza, "Determination of Moisture, Protein, Fat, and Calories in Raw Pork and Beef by Near Infrared Spectroscopy", Journal of Food Science, vol. 48, Issue 2, pp. 471-474, Mar. 1983.

Ng et al., "Characterization of the Fat Content of Beef using Microwave Techniques", European Microwave Conference, pp. 929-932, Oct. 9-12, 2007, Munich.

Schimmer et al., "UWB-sensors in Food Quality Management—the Way from the Concept to Market", International Conference on Ultra Wideband, pp. 141-144, Sep. 10-12, 2008.

Uddin et al., "Nondestructive Determination of Water and Protein in Surimi by Near-Infrared Spectroscopy", Food Chemistry, vol. 96, Issue 3, pp. 491-495, Jun. 2006.

Wang et al., "Quantitative Analysis of Fat Content in Rice by Near-Infrared Spectroscopy Technique", Cereal chemistry, vol. 83, Issue 4, pp. 402-406, Jul.-Aug. 2006.

* cited by examiner

*Primary Examiner* — Lisa Caputo
*Assistant Examiner* — Nasir U Ahmed
(74) *Attorney, Agent, or Firm* — Dority & Manning, P.A.

(57) ABSTRACT

A calorie estimating device for measuring a calorie content of a food item is provided. The device comprises a holder substrate, a transmitter antenna configured to transmit ultra-wide band (UWB) signals to at least a portion of the food item disposed on a side of the holder substrate, wherein the transmitter antenna comprises a planar antenna, a first receiver antenna configured to receive at least a portion of UWB signals reflected by the food item, wherein the first receiver antenna comprises a planar antenna, and a second receiver antenna configured to receive at least a portion of UWB signals propagated through the food item, wherein the second receiver antenna comprises a planar antenna.

27 Claims, 4 Drawing Sheets

SYSTEMS AND METHODS FOR NON-DESTRUCTIVELY MEASURING CALORIE CONTENTS OF FOOD ITEMS

BACKGROUND

The invention relates to systems and methods for measuring calorie contents of food items, and more particularly, to systems and methods for non-destructively measuring calorie contents of food items.

Due to health or other reasons it may be desirable to control one's weight. To effectively control weight, it is desirable to have a proper balance between caloric intake and number of calories burned. Whether a user is following a specific diet, a particular exercise regimen, is on weight gain/loss program or had a gastric bypass surgery, it is desirable to correlate calorie consumption with the number of calories burned. Even if the user wishes to merely maintain his/her weight, it is necessary to balance the number of calories consumed and the number of calories burned, as in this case both should be approximately same.

The calories are burned as a result of specific exercises/physical activities done by the user. In calculating the number of calories burned, the user takes into consideration the type of activity in which the user is engaged. The number of calories burned is a function of the level of activity and also dependent upon the particular characteristics of the individual, such as the weight, age and sex. To obtain the number of calories burned due to a specific exercise/physical activity the user may use available devices that enable automated monitoring of calories burned. For example, most modern exercise machines display an estimate of the number of calories burned during that particular exercise. Further, the user may use accelerometer based activity monitors to automatically translate daily body movements to the calories burned.

In recording the number of calories consumed, it is desirable that the user has some information readily available which indicates the number of calories per unit quantity of various food items that the user is consuming. Keeping track of calories consumed remains a fairly manual and time-consuming task. Typically, keeping track of the calories consumed requires the user to measure a weight or volume of each food item to be consumed and to find the calories of that particular food item from an index (either a book or online). Subsequently, the user has to then translate the index units to the amount of food eaten and record in a diet journal. Further, many of the food items eaten may not be accurately described by a value in the index. Also, the calorie content of the food items consumed varies widely depending on the ingredients and amounts of those ingredients. One way around this problem is to manually index each ingredient in a recipe and add them up; but this requires even more effort. The actual calorie content of a meal may vary widely depending upon the actual quantities of ingredients used in the preparation of the meal.

Some of the existing industrial approaches use a guided microwave spectrometer (GMS) for moisture and fat content analysis. In GMS method the sample chamber, where the food item will be disposed for measuring the moisture and fat content, is required to be filled completely with the food item to enable the spectrometry based measurements to be carried out. Although the food will occupy a portion of the sample chamber, due to varying shapes and sizes of the food items (e.g., fruits, vegetables, sandwiches, pizza slices, etc.), it may not be always feasible to fill the sample chamber with the food.

In addition, if the user needs to measure a calorie content of a meal, where the meal comprises two or more food items, the existing systems require that the calorie contents of the different food items be estimated one at a time. The existing systems are not configured to simultaneously estimate individual calorie contents of the two or more food items. Hence, making it time consuming to assess total calorie content of the meal.

There is therefore a need for a system and method that is suited for different food types and allows a user to get an empirical estimate of a calorie content of the food items of various shapes and sizes that the user plans to consume. In addition, there is a need for a system and method that allows the user to simultaneously estimate individual calorie contents of different food items, e.g., different items that comprise a meal.

BRIEF DESCRIPTION

In one embodiment, a calorie estimating device for measuring a calorie content of a food item is provided. The device comprises a holder substrate, a transmitter antenna configured to transmit ultra-wide band (UWB) signals to at least a portion of a food item disposed on a side of the holder substrate, wherein the transmitter antenna comprises a planar antenna, a first receiver antenna configured to receive at least a portion of UWB signals reflected by the food item, wherein the first receiver antenna comprises a planar antenna, and a second receiver antenna configured to receive at least a portion of UWB signals propagated through the food item, wherein the second receiver antenna comprises a planar antenna.

In another embodiment, an open cavity system for non-destructively measuring a calorie content of a food item is provided. The system comprises a calorie estimating device, and a processing unit operatively coupled to the calorie estimating device and configured to determine a calorie content of the food items based on the signals received by the first and the second receiver antennae. The calorie estimating device comprises a holder substrate having at least two sides, a transmitter antenna configured to transmit ultra-wide band (UWB) signals to at least a portion of a food item disposed on a side of the holder substrate, wherein the transmitter antenna comprises a planar antenna, a first receiver antenna configured to receive at least a portion of UWB signals reflected by the food item, wherein the first receiver antenna comprises a planar antenna, and a second receiver antenna configured to receive at least a portion of UWB signals propagated through the food item, wherein the second receiver antenna comprises a planar antenna.

In yet another embodiment, a method for non-destructively measuring individual calorie contents of one or more food items is provided. The method comprising irradiating the food items with UWB signals such that at least a portion of the UWB signals interact with the food items, acquiring at least a portion of signals reflected by the food item, acquiring at least a portion of signals propagated through the food item, estimating fat contents and water contents of individual food items based on the acquired reflected and transmitted signals, and determining individual calorie contents of the food items based on the estimated fat and water contents.

In another embodiment, a kit for measuring individual calorie contents of one or more food items is provided. The kit comprises a holder substrate having at least two sides, a transmitter antenna configured to transmit UWB signals to at least a portion of the food item disposed on a side of the holder substrate, wherein the transmitter antenna comprises a planar antenna, a first receiver antenna configured to receive at least a portion of UWB signals reflected by the food item, wherein the first receiver antenna comprises a planar antenna, and a second receiver antenna configured to receive at least a portion of UWB signals propagated through the food item, wherein the second receiver antenna comprises a planar antenna.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
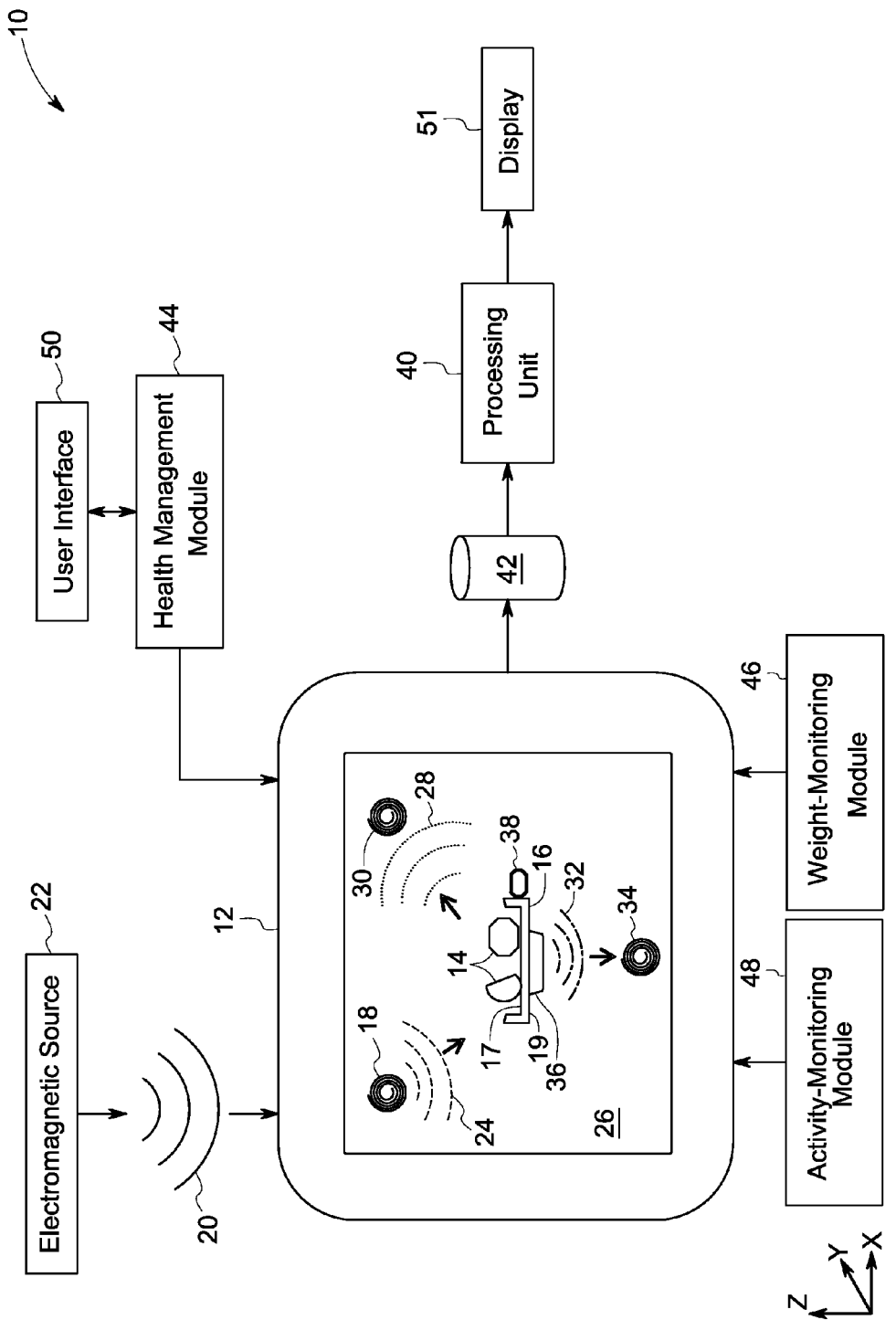
FIG. 1 is a schematic diagram of an example of a calorie estimating system for non-destructively measuring individual calorie contents of one or more food items.

Embodiments of the invention relate to systems and methods for non-destructively measuring individual calorie contents of one or more food items. In a case of two or more food items, the calorie content of the different items may be measured simultaneously. Advantageously, the systems and methods automatically measure the calorie content of the food items in a time efficient manner. In one embodiment, automatically measuring the calorie content may encompass, measuring the calorie content with least manual intervention once the food items are disposed in the calorie estimating system. For example, automatically measuring the calorie content may comprise simply placing a dish with a meal (one or more food items) in the calorie estimating device, and pressing a button to receive individual calorie contents of the food items that comprise the meal. The calorie estimating device may be incorporated into pre-existing appliances, such as but not limited to, microwave ovens and refrigerators. Alternatively, the calorie estimating device may be a stand-alone unit.

In certain embodiments, the calorie estimating device comprises a holder substrate, a transmitter antenna, a first receiver antenna and a second receiver antenna. The transmitter antenna is configured to transmit ultra-wide band (UWB) signals to at least a portion of a food item disposed on the first side of the holder substrate. The first receiver antenna is configured to receive at least a portion of UWB signals reflected by the food item. The second receiver antenna is configured to receive at least a portion of UWB signals propagated through the food item. The transmitter antenna, first receiver antenna and second receiver antenna are planar antennae. In one embodiment, the transmitter antenna, first receiver antenna and second receiver antenna may have same or different shapes and sizes.

In one embodiment, the calorie estimating device may also comprise a weighing scale to determine the mass of the item, a sensor to determine the position of the item, and a sensor to determine the temperature of the item. Weight, position and temperature of the food items may be used to yield relatively accurate estimations of the calorie contents of the food items.

In one embodiment, the position of the different food items may be determined by the receiving antennae.

To more clearly and concisely describe the subject matter of the claimed invention, the following definitions are provided for specific terms, which are used in the following description and the appended claims. Throughout the specification, exemplification of specific terms should be considered as non-limiting examples.

As used herein, the phrase "open cavity arrangement" refers to an arrangement that allows free space transmission of radiation, such as UWB signals.

As used herein, the term "move" refers to a translational movement, rotational movement, or both.

As used herein, the terms "rotational" or "rotate" encompass rotation in a range from about 0 degrees to about 360 degrees.

One or more food items for which the calorie contents are to be measured may be disposed in the calorie estimating system. The food items may be disposed on the holder substrate. The phrase "food items disposed on the holder substrate" refer to the food items being directly disposed on the holder substrate, or the food items being disposed on a dish, and the dish, in turn being disposed on the holder substrate. The transmitter antenna of the calorie estimating device may provide UWB signals for interacting with the food items. Further, the receiver antennae may receive the interacted UWB signals. In one example, the interacted signals may comprise signals that are reflected by the food items and signals that propagate through the food items. A processing unit may determine fat and water contents of the food items based on the received interacted UWB signals. A calorie content of the food items may be calculated based on the estimated fat and water contents. The calorie content of the individual food items may be determined using the methods and equations disclosed in earlier filed U.S. patent application Ser. No. 12/873,067 entitled "SYSTEM AND METHOD FOR MEASURING CALORIE CONTENT OF A FOOD SAMPLE".

In certain embodiments, the food items may be disposed in an open cavity arrangement to measure the calorie content. Advantageously, open cavity arrangement eliminates the need to fill the cavity with the food items for which the calorie content is to be measured. Hence, the calorie content of different food items may be measured irrespective of shapes, sizes, and amount of the food items. For example, since there is no need to fill the cavity with the food items, calorie contents of relatively smaller amounts of food items may be measured. Further, the open cavity arrangement enables in-situ measuring of the calorie content of the food items. For example, if the food is already served in a dish, the calorie estimating system enables calorie measurement without disturbing the food items on the dish. For estimating calorie content, after serving the food items in a dish (e.g., plate or cup), the dish having the food items may be disposed on the sample holder.

In embodiments where two or more food items are disposed on the holder substrate, the food items as a whole may constitute an inhomogeneous material. Fat and water contents of the inhomogeneous material, such as a meal comprising a plurality of food items, may be estimated. In one embodiment, the calorie contents of the individual food items of this inhomogeneous material may be estimated and displayed. In one embodiment, the calorie content of the entire meal may be displayed. The calorie content of the entire meal may be a summation of the individual calorie contents of the food items In certain embodiments, estimated calorie contents of the food items may be derived by measuring properties of signals that are reflected and transmitted from the food items. The emitted UWB signals comprise associated wave parameters, such as but not limited to, amplitude, a phase, attenuation, time delay, spectral content, and a phase shift. As the emitted UWB signals travel from the transmitter antenna to the receiver antennae and transmit through the food items (and the holder substrate and/or the dish), the wave parameters of the propagating signals are perturbed due to the presence of the food items. Changes in the parameters associated with the signals due to interactions with the food items may therefore provide information about the complex dielectric constant of the food items.

The food items constitute a dispersive transmission path for the transmitting UWB signals. An irregular surface of the food items and non-homogeneous distribution of the material on dish or the holder substrate may also contribute to dispersion of the UWB signals. For example, the time of arrival of a transmitted wave at the second receiver may be dependent upon a thickness of the food item. For the UWB waves propagating through a free space region of the calorie estimating device, the wave parameters may be determined as a function of the geometry of the free space region and the properties of the transmitter antenna.

The UWB signals transmitted through the food items may be distorted, delayed and attenuated by having traveled through the material of the food item. For example, as the UWB signals interact with the food items, polar molecules disposed in the water and fat in the food item may rotate so as to align with the electromagnetic field associated with the propagating wave, this rotation affects the properties of the signals. In one embodiment, the rotational movement may also comprise oscillatory movement. Measurements of pulse transmission delay and attenuation are directly related to the complex permittivity. The width of this transmitted pulse may be a function of the shape of the surface of the material. The amount of time delay in the UWB signals and the amount of attenuation in the UWB signals is a function of the electrical properties of the material through which the UWB signals transmit thought to reach the second receiver antenna.

Time of flight of electromagnetic waves, such as UWB signals, through food is very fast, hence, a sharp or narrow pulse is desirable for accurately determining the time of flight of the UWB wave in the food item. In one example, a pulse width of such a pulse may be less than about 100 pico seconds. A narrow pulse corresponds to a wider or higher bandwidth. A higher bandwidth provides enhanced resolution for smaller time delays in the travel of the UWB signals at the receiver antennae. In one embodiment, bandwidths of 2 GHz and more may be desirable to determine time to flight of the UWB signals in the food items. In one embodiment, the system may operate in a frequency range from about 100 MHz to about 20 GHz. In one embodiment, the system may operate in a frequency range from about 100s of MHz to about 6 GHz. The minimum frequency may be dependent on the size of the transmitter antenna. In this embodiment, the transmitter antenna may be configured to emit UWB signals in a range from about 2 GHz to about 20 GHz.

High bandwidth requirements pose challenges for antenna designs. Typically, large sized antennae are required to accommodate lower frequencies in the bandwidths. Employing large antennae results in large devices and systems. Such large systems may pose challenges at least with respect to space requirements. Further, it may not be feasible to accommodate large antennae in home appliances, such as but not limited to, microwave ovens and refrigerators. Hence, compact antennae are desirable to suit the space constraints, e.g., of the home appliances. In one example, a calorie estimating device employing small sized antennae may be easy to retrofit in an existing home appliance.

In certain embodiments, the transmitter antenna, first receiver antenna and second receiver antenna may comprise one of a linear, an elliptical or a circular polarization. The circular and elliptical polarizations may comprise a left hand or right hand polarization. The transmitter antenna, first receiver antenna and second receiver antenna may have same or different polarizations. In one embodiment, the transmitter antenna, first receiver antenna and second receiver antenna may comprise a circular polarization. In one embodiment, the transmitter antenna may have a different polarization than the first and second receiver antennae. The polarization of the antennae may be selected based on factors such as but not limited to, antenna geometry, ease of production of the particular polarization type.

The circular polarization facilitates reduction or elimination of spurious signals from various undesirable surfaces within the device. For example, the reflected signals from various undesirable surfaces may lose the circular polarization characteristics and may not be detected by the receiver antennae. Non-limiting examples of spurious signals may comprise reflections from walls of the appliance, such as a microwave oven, in which the food items are disposed.

In one embodiment, the variations in the parameters of the UWB signals may be addressed by minor modifications in the designs of the antennae. For example, the antennae may be designed to produce more uniform field over the area of the dish (e.g., food plate).

In certain embodiments, the planar antenna may comprise a two-dimensional (2D) antenna. In these embodiments, windings of the planar antenna are disposed in one plane. The planar antenna may comprise a spiral antenna. In one embodiment, the spiral antenna may be a frequency independent antenna that is configured to operate over a wide range of frequencies. The spiral antenna may be configured to cover relatively higher bandwidth than its linear counterpart, while maintaining compact size. That is, the spiral antenna may have good spectral efficiency. Polarization, radiation pattern and impedance of a spiral antenna may remain mostly unchanged over a wide bandwidth. In one embodiment, one or more of the transmitter antenna, first receiver antenna, or the second receiver antenna may comprise an array of spiral antennae. The array of the spiral antennae may be used to increase the gain of the antennae. Spiral antennae provide compact, cost efficient and effective options. In one embodiment, the outer diameter of the antenna may be in a range from about 5 cm to about 10 cm. In this embodiment, the spiral antenna may comprise relatively lower aspect ratio (height:diameter). In one example, the aspect ratio of the spiral antenna may be in a range from about 0.5 to about 1.

The planar antenna may comprise different shapes, such as but not limited to circular, elliptical, rectangular, square, triangular, or any other geometrical or irregular shape. The shape of the planar antenna may be dictated by the ease of fabrication processes. In one embodiment, the planar antenna may comprise a patch antenna. The patch antenna may be configured to be mounted on flat or curved surfaces. The patch antenna may comprise an assembly having a sheet (patch) of metal, mounted over another sheet of electrically conductive surface. The assembly may be disposed in a non-conductive enclosure to protect the assembly from any damage due to environmental factors. The assembly and enclosure may be disposed on a substrate. The substrate may be made of a dielectric material. In one example, the patch antenna comprises a metal foil spiral pattern etched on a dielectric substrate.

In certain embodiments, it may be desirable to acquire data from the different parts of the food items (as opposed to a single place or point). In some embodiments, the food items disposed on the holder substrate may be scanned. In other embodiments, the entire volume of the food items may be irradiated with the UWB signals. In instances where two or more food items are disposed on the holder substrate, scanning or irradiating the volume of the different food items with the UWB signals enables simultaneously estimating individual calorie contents of the different food items.

In one embodiment, the different food items may be irradiated by employing a plurality of transmitter antennae that are configured to irradiate different portions of the food items. The use of the plurality of transmitter antennae may facilitate irradiating the volume of the food items without scanning the food items by the UWB signals. In another embodiment, one or more transmitter antennae may be employed to enable scanning of the volume of the food items by the UWB signals. In one embodiment, a plurality of first and/or second receiver antennae may be employed to receive UWB signals from the different food items. The plurality of first and/or second receiver antennae may be employed in combination with the plurality of transmitter antennae. Alternatively, the plurality of first and/or second receiver antennae may be employed when scanning the food items.

The transmitter antenna and/or the holder substrate may be configured to move along or about an x-axis, y-axis, z-axis, or combinations thereof to scan the food items. In these embodiments, the first receiver antenna, second receiver antenna, or both may be configured to move along or about the x-axis, y-axis, z-axis, or combinations thereof to receive the reflected and propagated UWB signals from the food items.

The holder substrate, transmitter antenna, or both may undergo translational and/or rotational movements to enable scanning of the food items. In one embodiment, the holder substrate, transmitter antenna, or both may translate along one or more of an x, y, or z-axis to enable scanning of the food items. In another embodiment, the holder substrate, transmitter antenna, or both may rotate about the x, y, z-axis, or combinations thereof to enable scanning of the food items. The rotating and/or translating speeds of the holder substrate, transmitter antenna, or both may be same or different. In one example, the holder substrate may rotate, and the transmitter antenna may translate, or vice versa.

In certain embodiments, the first and/or second receiver antennae may be configured to translate and/or rotate to receive interacted UWB signals from the food items during scanning or irradiating the volume of the food items. The movements of the holder substrate, transmitter antenna, or the first and/or second receiver antennae may be enabled by operatively coupling a motor with the holder substrate, transmitter antenna, or the first and/or second receiver antennae. In one embodiment, the motor may be a stepper motor. A stepper motor is usually compact in size and is an electromagnetic device that converts electric pulses into discrete mechanical motion.

In case of home applications, the different appliances configured to estimate the calorie content may be in operative association with each other and with a centralized processing unit. The centralized processing unit may help the user keep track of their intake at least for the meals consumed at home. The centralized processing unit may be configured to separately process, store and display information regarding one or more members in the house.

In certain embodiments, the calorie estimating device may be provided as a kit that may be retrofitted in existing appliances, such as but not limited to, microwave oven, or refrigerator, thereby adapting the existing appliances to estimate calorie content of food items in addition to performing the regular functions of the appliances.

The user-friendly nature of the system facilitates re-accessing the calorie content. For example, if the calorie content of the food items in the dish is beyond an acceptable value for the user, the type and/or quantity of food items may be adjusted, and the calorie content may be re-assessed. This process may be continued until a desirable range of the calorie content is reached. Further, high data rates and low power requirements of UWB systems make them feasible for portable commercial applications.

FIG. 1 is a block diagram of a system for non-destructively measuring a calorie content of one or more food items. The system 10 comprises a calorie estimating device 12. The calorie estimating device 12 may comprise an open cavity configuration. The calorie estimating device 12 may comprise a holder substrate 16 having a first side 17 and a second side 19. In one embodiment, the food items 14 may be directly disposed on the holder substrate 16. In an alternate arrangement, the food item may be disposed in a dish (not shown) and the dish may in turn be disposed on the holder substrate 16. In one embodiment, the holder substrate 16 may be configured to undergo rotational and/or translational movements along or about one or more x, y and z-axis. The movements may facilitate scanning of the food items by the incident UWB signals. In one example, the holder substrate 16 may be a base plate of the microwave that is configured to undergo rotation, e.g., to evenly warm the food items 14.

The estimating device 12 further comprises a transmitter antenna 18 that is disposed facing the first side 17 of the holder substrate 16. The transmitter antenna 18 is configured to transmit UWB signals, generally represented by the reference numeral 24, in a free space region 26 of the device 12, such as a microwave. At least a part of the transmitted waves 24 is transmitted to the food items 14.

The holder substrate 16 and the transmitter antenna 18 are configured to enable scanning of the volume of the food items 14 disposed on the holder substrate 16. In one embodiment, two or more transmitter antennae may be used. The use of plurality of transmitter antennae may facilitate scanning of the food items 14 without the need for rotational or translational movements of the holder substrate 16 or transmitter antenna 18. In one embodiment, the plurality of second receiver antennae may be disposed in a linear configuration or an array configuration. In one embodiment, the transmitter antenna 18 is configured to undergo translational or rotational movements to scan the volume of the food items 14. In another embodiment, the holder substrate 16 may be configured to provide rotational or translational movements to enable the food items 14 to be scanned by the radiation 20 emitted by the transmitter antenna 18.

The system 10 may further comprise first and second receiver antennae 30 and 34, respectively. In some embodiments, the first receiver antenna 30 may be disposed facing the first side 17 of the holder substrate 16. The first receiver antenna 30 may be disposed on the same side of the holder substrate 16 as the transmitter antenna 18. The second receiver antenna 34 may be disposed facing the second side 19 of the holder substrate 16. The second receiver antenna 34 may be disposed on the opposite side of the holder substrate 16 than the transmitter antenna 18 and the first receiver antenna 30. The first receiver antenna 30 may be used to receive the UWB signals 28 that are reflected by the food items 14, holder substrate 16, or the dish (not shown) in which the food items 14 are disposed. The second receiver antenna 34 may receive UWB signals 32 that propagate through the food items 14.

In certain embodiments, two or more receiver antennae may be configured to receive UWB signals that are reflected or transmitted by the food items 14. In another embodiment, the calorie estimating device 12 may comprise a plurality of first and/or second receiver antennae 30 and 34, respectively. In one example, the plurality of first receiver antennae may be employed to receive at least a portion of the waves 28 reflected from the food items 14 during the scanning of the food items 14. The plurality of first receiver antennae may be disposed on the same side of the holder substrate 16 as the transmitter antenna 18. In one example, the plurality of second receiver antennae may be employed to receive at least a portion of the waves 32 propagating through the food items 14 during the scanning of the food items 14.

In one embodiment, a single antenna may function as a transmitter and receiver antenna. In this embodiment, the transmit/receive antenna or the transceiver antenna may be used as the transmitter antenna 18 as well as the first receiver antenna 30. Such an antenna may transmit UWB signals to the portion of the food item and receive at least a portion of the UWB signals reflected by the food items 14.

In one embodiment, the first receiver antenna 30, the second receiver antenna 34, or both are configured to translate and/or rotate. The translational or rotational speed of the receiver antennae 30 and 34 may be decided based upon the scanning speed of the food items 14. The displacement speeds of the receiver antennae 30 and 34 may be adjusted according to the scanning speed of the transmitter antenna 18. In one example, both the transmitter antenna 30 and the holder substrate 16 may be configured to undergo translational and/or rotational movements.

Scanning or irradiating the different food items 14 with the UWB signals may be particularly useful when two or more different food items are disposed on the holder substrate 16. The scanning provides spatially oriented calorie information for the food items 14. The scanning information may be mapped to different parts of the holder substrate 16 to form an image of the food items. The image of the food items may be useful in indicating calorie information for different parts of the food items. To that end, if a food item disposed in a plate comprises two different items, e.g., pizza slice and baked potatoes, scanning of the food items enables individual quantification of calories for the different food items placed in the dish or the holder substrate 16. Therefore, a person deciding to consume more than one type of food items is able to measure the calorie content of the different food items in a single step and is not required to perform the calorie measurement step for the different food items separately.

In one embodiment, the calorie estimating device 12 may comprise a weighing device 36. The weighing device 36 may be coupled to the holder substrate 16. In one embodiment, the weighing device 36 may be a weighing scale or a weight sensor. In one example, the weighing device 36 may be integrated into the microwave oven.

In another embodiment, the calorie estimating device 12 may comprise a temperature measuring device 38, such as, for example, a thermometer, a thermocouple, an infrared thermometer, or a temperature sensor for measuring a temperature of the food items 14.

When the system 10 is switched on, the transmitter antenna 18 transmits signals 24 to the food items 14. The UWB signals 24 may be generated by an electromagnetic source 22 and a portion of the generated signals 20 may be transmitted to the transmitter antenna 18.

Some of the incident signals 24 may be reflected by the holder substrate 16, the dish or the food items 14. At least a portion of the reflected signals 28 are received by the first receiver antenna 30. In addition to being reflected, some of the incident signals 24 are transmitted through the food items 14. At least part of the transmitted signals 32 are received by a second receiver antenna 34.

The data collected by the antennae 30 and 34 in the form of reflected and propagated signals representative of a complex dielectric constant of the food items 14. The collected signals enable subsequent estimation of the fat and water content, and hence, the calorie content of the food items 14. The data collected by the calorie estimating device 12 may be transmitted to a processing unit 40 for subsequent use in estimation of the fat content and the water content of the food items 14 and calculation of the calorie content of the food items 14.

The UWB signals travelling from the transmitter antenna 18 to the receiver antennae 30 and 34 may be affected by various system variables, including, for example, the total mass, volume, density, geometry, and temperature of the food items 14. The extent to which these variables may affect the UWB signals may depend, for example, on the uniformity of the electromagnetic field associated with the UWB signals. The processing unit 40 of the estimating device 12 may be configured to calibrate readings of the estimated fat and water content for varying total mass, volume, density, and temperature of the food item.

Each of the transmitter antenna 18, first receiver antenna 30, second receiver antenna 34, weighing device 36, and temperature measuring device 38 may be operatively coupled to the processing unit 40. The processing unit 40 may comprise a computer, smartphone, network analyzer, or the like, that may be coupled to the calorie estimating device 12. The data collected may be stored in a memory 42 (e.g., RAM) that is operatively coupled to the calorie estimating device 12 and the processing unit 40. The memory 42 may store data collected by the calorie estimating device 12 and/or data processed or to be processed by the processing unit 40.

The system 10 may further comprise a health management module 44. The health management module 44 may comprise a computing device, such as, for example, a computer, a smartphone, and/or the like, which may be configured to execute a health management application. The computer may comprise hardware that is configured to execute the health management application, such as an application-specific integrated circuit, or may comprise or receive (say, via the Internet) instructions (e.g., software) to be executed by a general-purpose central processing unit of the computer. In any event, the health management application, when executed, may present a graphical user interface that enables a user to track his or her weight, the calories consumed, and the calories burned in real time. The health management module 44 may communicate with a storage device, such as, for example, a random access memory. The storage device may be either integral to the health management module, or may be located remotely and accessible, e.g., via a local network and/or the Internet. In one embodiment, software associated with the health management application may be stored in the storage device. The health management module 44 may comprise a wireless transmitter/receiver that may facilitate uploading data from various external sources to the health management module 44.

The health management module 44 may provide means for a user, on a real time basis, to track the calories that have been burned while simultaneously providing a means for tracking the calories in the food items 14 that the user is planning to consume. This system could therefore afford the user the ability to make competent and rational dietary and exercise decisions by timely comparisons of dietary and exercise activities.

The system 10 may further comprise a weight-monitoring module 46 and an activity-monitoring module 48. The weight-monitoring module 46 may comprise a simple weighing scale to measure the weight of the user, and/or may comprise a machine configured to measure the Body Mass Index (BMI). The activity-monitoring module 48 may comprise an automated monitor to track the calories burned by the user. In one embodiment, the activity-monitoring module 48 may comprise a wearable device, such as, for example, a pedometer, a three-dimensional accelerometer, a heart rate monitor, and/or the like. The activity-monitoring module 48 may be suitably calibrated so as to convert measurements of activity into calories burned.

The calorie estimating device 12 may be operatively coupled to the health management module 44, the weight-monitoring module 46, and/or the activity-monitoring module 48, say, via a wireless device. The calorie estimating device 12, the weight-monitoring module 46, and/or the activity-monitoring module 48 may therefore transmit data collected thereby to the health management module 44, for example, so as to be stored by a storage device. Aside from weight and calorie consumption data, the storage device may also retain historical health data.

A user interface 50 may be communicatively coupled to the health management module 44 and may provide an indication of weight/BMI information obtained from the weight-monitoring module 46, calorie content obtained from the calorie estimating device 12, and the burned calories obtained from the activity-monitoring module 48. The user interface 50 may be, for example, a wearable device or an electronic card that allows the user to view the calories consumed and the calories burned throughout the day. It should be further noted that the user interface 50 and the activity-monitoring module 48 may exist as an application running on a single wireless device, such as a cellular telephone, a portable computing device (e.g., a smart phone, a laptop computer, or an application-specific device), etc., which computing device may coincide with the computing device of the health management module 44. The information on the calorie content of the food items 14 may be uploaded via the wireless transmitter to the health management module 44.

In one example, the calorie estimating system 10 may be configured to allow a user to enter a command (e.g., by pressing a button) that results in a signal being sent by the processing unit 40 to the device 12 to initiate the transmission of the UWB signals from the transmitter antenna 18. The command may be entered using the user interface 50.

The estimated individual calorie contents of the food items may be displayed. The individual calorie contents of the food items may be displayed along with the acquired sample representations. The data may be displayed on a visual display device 51, such as a video monitor, and visually observed to obtain information concerning properties of the substance. For example the visual display may show the amplitude and shape of the received pulses as a function of time. In one embodiment, an image may be formed of the food items disposed in a plate. The image may comprise an illustration of different food items disposed on the holder substrate and their respective calorie contents. Optionally, the images of food items themselves may be labeled to indicate their respective calorie content values.

Figure 2:
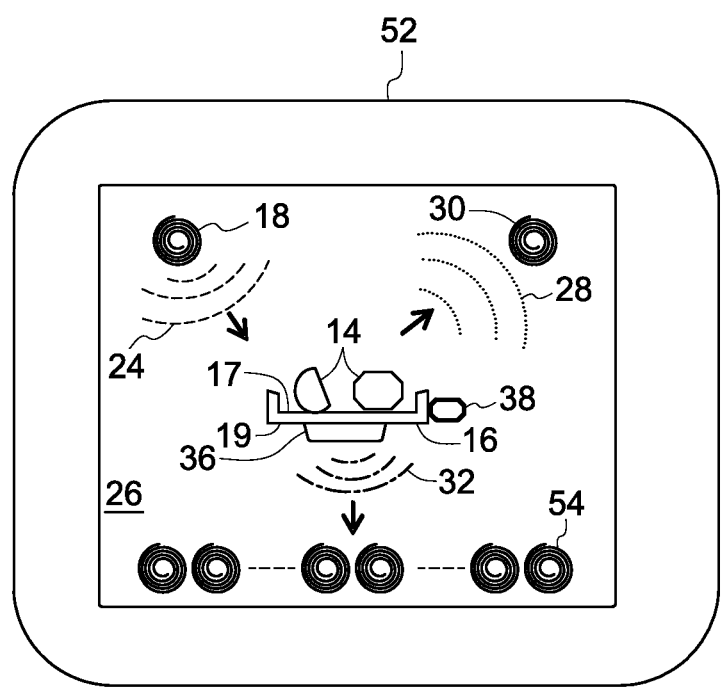
FIG. 2 is a schematic diagram of an example of a calorie estimating device comprising a plurality of second transmitter antennae that are configured to receive ultra-wide band signals transmitted through the food items.

FIG. 2 illustrates an alternate embodiment of the calorie estimating device of FIG. 1. In the illustrated embodiment, a calorie estimating device 52 comprises a plurality of second receiver antennae 54. The plurality of second receiver antennae 54 are configured to receive at least a portion of the radiation that propagates through the food items 14. In one embodiment, the plurality of second receiver antennae 54 may be used in combination with a plurality of transmitter and/or receiver antennae. In one example, the plurality of second receiver antennae 54 may be used to acquire data during scanning of the food items 14.

Figure 3:
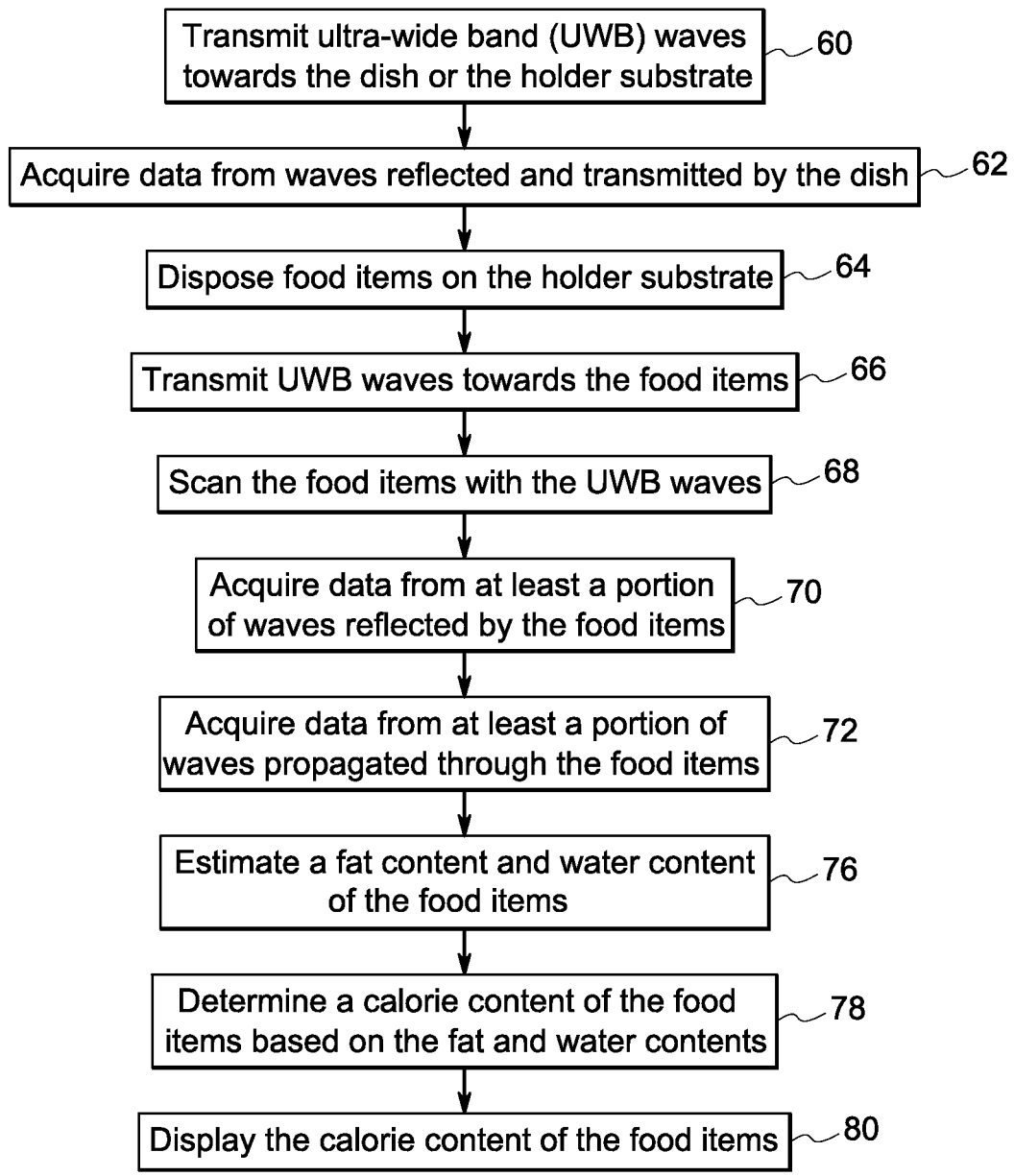
FIG. 3 is a flow chart of an example method for measuring individual calorie contents of one or more food items.

FIG. 3 illustrates a flow chart of an example method for measuring individual calorie contents of one or more food items disposed in a calorie estimating device. The measurements are performed with and without food items. The information regarding the measurements without food items may be pre-stored in the system. For example, the information regarding the time of travel, amplitude, of the signals may be stored in a memory that is accessible to the processing unit.

At step 60, UWB signals are transmitted and directed towards the holder substrate, the food items are not disposed on the holder substrate. In one example, a dish without the food items may be disposed on the holder substrate and the UWB signals may be directed towards the dish. At step 62, data are acquired from UWB signals reflected by the holder substrate, dish, or both. Data are also acquired from UWB signals transmitted through the holder substrate, dish, or both.

At step 64, food items are disposed on the holder substrate; alternatively, a dish having the food items may be disposed on the holder substrate. At step 66, UWB signals are incident on the food items. In one example, a transmitter antenna may selectively transmit UWB signals into the free space region of the open cavity spectrometer of the calorie estimating device. The transmitter antenna may be disposed such that majority portion of the UWB signals transmitted by the transmitter antenna is directed towards the food items.

At step 68, the food items are scanned using the UWB radiation. Alternatively, the volume of the different food items may be irradiated using a plurality of transmitter antennae. The scanning may be performed to map calorie content information with respect to different portions of the food items. In instances where calorie contents for two or more different food items need to be measured simultaneously, the scanning may be used to provide separate calorie content information for the different food items. The scanning may be performed by moving the transmitter antenna along or about an x, y, or z-axis to adjust the direction of the radiation transmitted by the transmitter antenna. Alternatively, the scanning may be performed by moving the holder substrate disposed thereon along or about an x, y, or z-axis.

In one embodiment, a frequency domain scan may be performed. In another embodiment, a time domain scan may be performed. The frequency domain scan may comprise using swept frequency radiation. The time domain measurements may comprise using pulsed radiation. The pulse of electromagnetic radiation in time domain is equivalent to a wide frequency band signal in frequency domain. The low frequency and high frequency components of the UWB signals may be related to specific characteristics of materials of the food items.

In some embodiments, the UWB signals transmitted by the transmitter antenna may be in the form of one or more pulses. In one embodiment, short pulses characterized by time durations of few sub-nanoseconds may be transmitted to the food items. The time duration of a pulse of energy and the frequency bandwidth of the energy spectrum of the pulse are inversely related. That is, shorter the duration of the pulse, the wider is the band of frequencies of energy comprising the pulse. Therefore, the frequency spectrum of a narrow input pulse may comprise broad energy spectrum. Thus, a sufficiently narrow UWB pulse may exhibit a broad frequency spectrum of energy. The broad frequency spectrum of energy interacts with the food items over a desirable frequency range. In one embodiment, the UWB signals comprise a pulsed signal having a plurality of pulses. The plurality of pulses may be successive pulses that are spaced in time. The pulses may be uniformly or non-uniformly spaced in time. The timing of the pulses in the repetitive sequence may be at a regular spacing according to a fixed pulse repetition frequency. That is, the time intervals between successive pulses may be substantially equal. Alternatively, pseudo-random or other non-uniformly spaced pulses may be used. A non-uniform spacing may be selected to distribute the various frequency components in the pulse sequence over a broad band of frequencies such that the broad band of frequencies may appear as a low level noise spectrum to other electronic equipment that could otherwise be affected by stray emissions.

In other embodiments, the UWB signals transmitted by the transmitter antenna may comprise sweep frequencies. The swept frequency measurements are equivalent to transmitting an electromagnetic pulse in time domain. In one embodiment, an inverse Fourier transform (IFT) of the swept frequency measurements may be calculated to obtain time domain and pulsed measurements. In embodiments where swept frequency measurements are employed, start frequency and stop frequency of the sweep frequencies may be adjusted to set the bandwidth. Setting a desirable bandwidth allows selection and optimization of the bandwidth to enhance sensitivity for specific applications. For example, the bandwidth may be optimized to suit particular food types. Once an optimized bandwidth is determined, IFT may be used to work in the time-space and shape a UWB pulse with appropriate pulse widths and amplitude profiles. When using swept frequency measurements, the start and finish frequencies may be smoothly change from specified start and finish frequencies. The rate at which the values of start and finish frequencies may be changed may be linear or logarithmic. Setting the stop frequency above or below the start frequency may vary the direction of the sweep. In one embodiment, the sweep frequency may be a stepped sweep that comprises shifting from the start frequency by a set incremental frequency until the stop frequency is reached. In another embodiment, complex pattern sweeps may be generated using frequency modulation.

A portion of incident UWB signals on the food items are reflected, and a portion may be transmitted through the food items. At step 70, at least a portion of the UWB signals reflected or scattered by the food items are acquired. For example, the UWB signals may be received by a first receiver antenna. The time of arrival of the reflected pulses at the first receiver antenna may be dependent upon a thickness of the food items. The transit time of the signals reflected by the food items may provide information about thickness values of the food items disposed on the holder substrate. The transit time information together with the width of the received pulse is a function of the shape of the surface of the material. The thickness of the food items may vary from one position to another on the holder substrate. The variation in thickness of the food items may be plotted with respect to the position of the food items on the holder substrate. In one embodiment, the signals reflected by the food items may comprise signals reflected by the dish in which the food item is disposed or the holder substrate on which the food item is disposed. This information is processed by the processing unit to obtain information regarding the thickness and shape of the food items.

At step 72, at least a portion of the UWB signals propagated through the food items are acquired. In one example, the UWB radiation/signals propagated through the food items are received by the second receiver antenna. The properties of the propagated UWB signals may change due to travelling through the dispersive medium of the food items, for example, shape, phase, and time of arrival of the energy pulses at the receiver antennae. The properties of the signals may change according to the dimensions and content (electrical properties) of the food items. In one embodiment, the signals transmitted through the food items may be delayed and attenuated. The amount of time delay and the amount of attenuation may be a function of the electrical properties of the material through which the signals pass to reach the second receiver antenna.

At step 76, fat and water contents of the food items may be estimated by analyzing the reflected and transmitted signals. The acquired reflected and transmitted signals may be analyzed in time or frequency domains. A signal that varies as a function of time may be represented by a corresponding signal that varies as a function of frequency. Either representation may comprise equivalent information. The time and frequency signals are mathematically related by a Fourier transform. In one example, the Fourier transform may resolve a continuous-time signal into a continuous-frequency spectrum. In one embodiment, the acquired data may be converted to a frequency-domain representation using a Fast Fourier Transform (FFT) algorithm prior to further analysis. The FFT transforms the acquired data into a discrete frequency spectrum. Comparison between measurements obtained with and without food item provides measurement values for the complex dielectric constant and loss of the value in dielectric constant in the food item. For example, the comparison may enable determination of the magnitude of the perturbation of wave parameters of the signals due to the interaction of the signals with the food items. The complex permittivity values may be calculated from the complex dielectric constants. Measurements of pulse transmission delays and attenuation of wave parameters are directly related to the complex permittivity. Reflected and transmitted waves from the food items may be analyzed sequentially or simultaneously. In embodiments where the reflected and transmitted waves are analyzed simultaneously, the thicknesses of the food items may be calculated from the reflected data. In one example, the difference in the time of arrival of pulses at the corresponding receiving antenna without food and with food may be used to determine the thickness of the food item. The thickness values and the transmitted wave parameters may be used to calculate other values such as a complex dielectric constant, conductivity (mobile polar media—e.g. salt) variations between the with and without food data.

In one example, the transit time of the signals transmitted through the food items provides information about the complex dielectric constant of the food items when the thickness of the item is known. In addition, amplitude of the transmitted signals provides information about the electrical conductivity of the food item. The fat and water content of the items measured may be determined from the dielectric constant. For example, shape, size, fat content and water content of the food item may be calculated, when the dielectric constant is calibrated to the item's temperature.

In the case of a plurality of food items, the fat and water contents may be estimated separately for individual food items. Alternatively, cumulative fat and water contents may be estimated for the entire meal. The fat and water contents may be estimated, for example, by the processing unit after receiving wave data from the transmitter and receiver antennae. In one example, differences in the transmitted and received wave parameters may be analyzed to determine fat and water contents of the food items. In one embodiment, prior to estimating the fat and water contents of the food items, the acquired wave data may be calibrated for weight, volume, density, and/or temperature of the food items.

At step 78, a calorie content of the individual food items or the meal may be determined. The estimated calorie content may be displayed (step 80). In one embodiment, the displayed data may comprise information on the type of food item, and the calorie contents may be mapped to the corresponding food item.

Figure 4:
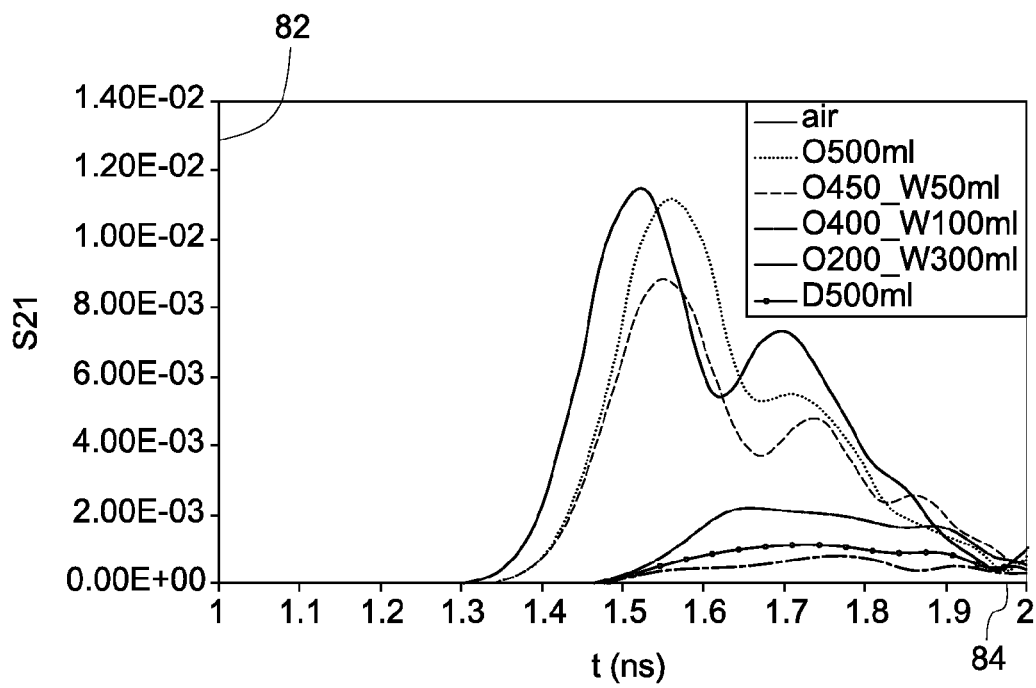
FIGS. 4-5 are graphs representing S21 parameters vs. time delays of ultra-wide band signals transmitted through mixtures comprising oil and water in various ratios.
Figure 5:
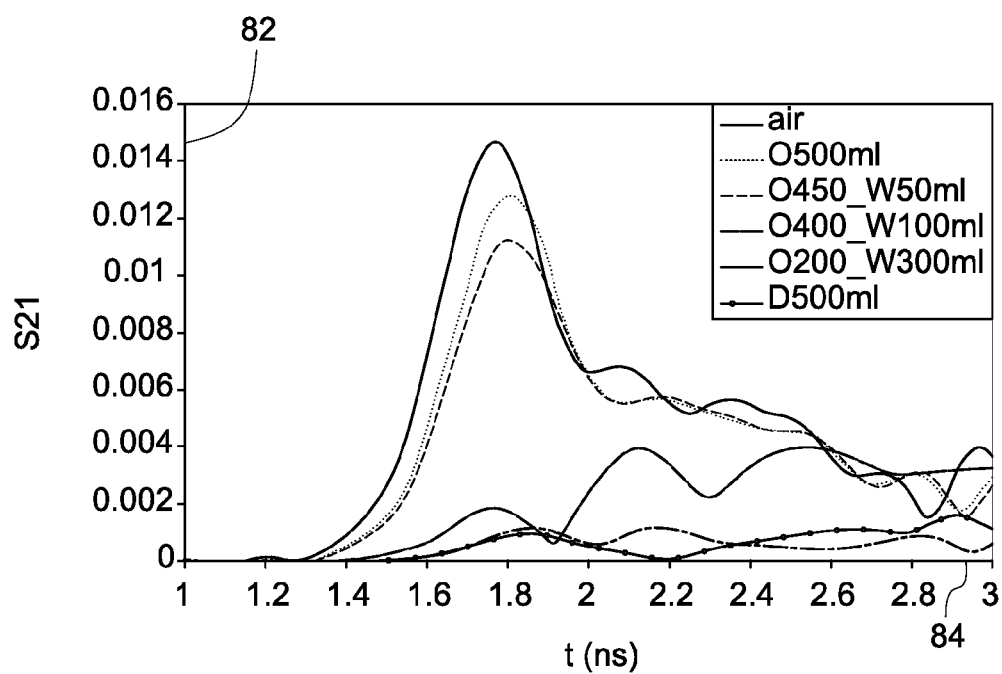

FIGS. 4-5 are example plots illustrating S parameters for oil and water mixtures. The mixtures comprise air, 500 ml oil, 450 ml oil+50 ml water, 400 ml oil+100 ml water, 200 ml oil+300 ml water, and 500 ml water. As illustrated, the mixtures with different ratios of oil and water have different effects on the UWB pulses. For example, the reflected and propagated signals from the different mixtures exhibit different time delays and attenuation values. These values contain the dielectric and geometric information of the food items that may be converted into calorie content. Abscissa 82 represents S21 component of the S parameters, ordinate 84 represents time delays of the interacted UWB signals. S21 component is a component of S parameter that is a measure of received signal at port 2 (receive antenna) when transmission is from port 1 (transmit antenna). FIGS. 4-5 represent two different frequency bandwidths used for calorie measurements. The frequency bandwidth of FIG. 4 is 16 GHz with the frequency in a range from about 2 GHz to about 18 GHz, and the frequency bandwidth of FIG. 5 is 8 GHz with the frequency in a range from about 2 GHz to about 10 GHz. The different bandwidths determine time resolution and the length of the pulse of the UWB signals. The higher the bandwidth, the narrower is the pulse. In the illustrated example of FIG. 4, the bandwidth of 16 GHz comprises a 0.7 ns pulse width with a pulse interval in the range from about 1.3 ns to about 2 ns. In the illustrated example of FIG. 5, the bandwidth of 8 GHz comprises a 1.7 ns pulse width with a pulse interval in the range from about 1.3 ns to about 3 ns. By using higher bandwidths (FIG. 4) the smaller time delays in the travel of the pulses may be resolved more effectively.

Advantageously, the systems and methods of the invention allow the fat and water content of one or more food items to be estimated simultaneously, without disturbing (non-contact) or destroying the food items. The calorie content may be measured for relatively smaller amounts of food items than calorie determinations in an industrial setting. The invention enables the user to automatically and simultaneously estimate calorie content of the one or more food items. The calorie content of the food items may be estimated just before consumption. Further, the existing devices may be modified to incorporate the calorie estimating device of the claimed invention. Estimation of the calories of the food item may be available simply by pressing a button. As such, these systems may be well suited for integration with conventional microwave-cooking devices.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A calorie estimating device for measuring a calorie content of a food item, comprising:
a holder substrate;
a transmitter antenna configured to transmit ultra-wide band (UWB) signals to at least a portion of the food item disposed on a side of the holder substrate, wherein the transmitter antenna comprises a planar antenna;
a first receiver antenna configured to receive at least a portion of UWB signals reflected by the food item, wherein the first receiver antenna comprises a planar antenna;
a second receiver antenna configured to receive at least a portion of UWB signals propagated through the food item, wherein the second receiver antenna comprises a planar antenna; and
wherein the device non-destructively measures the calorie content of the food item by comparing the received signals from the first receiver and the second receiver, measured both with and without the food item disposed on the holder substrate.

2. The calorie estimating device of claim 1, wherein the transmitter antenna, holder substrate, or both are configured to move along or about an x-axis, y-axis, z-axis, or combinations thereof.

3. The calorie estimating device of claim 1, wherein the device comprises an open cavity arrangement.

4. The calorie estimating device of claim 1, wherein one or more of the transmitter antenna, first receiver antenna, and second receiver antenna comprise a two-dimensional antenna.

5. The calorie estimating device of claim 4, wherein the two-dimensional antenna comprises a spiral antenna.

6. The calorie estimating device of claim 1, wherein the planar antenna comprises a circular shape, an elliptical shape, a rectangular shape, a square shape, or combinations thereof.

7. The calorie estimating device of claim 1, wherein one or more of the transmitter antenna, first receiver antenna, and second receiver antenna are configured to move along or about an x-axis, y-axis, z-axis, or combinations thereof.

8. The calorie estimating device of claim 1, wherein the transmitter antenna and the first receiver antenna are disposed facing same side of the holder substrate.

9. The calorie estimating device of claim 8, wherein the second receiver antenna is disposed facing another side of the holder substrate.

10. The calorie estimating device of claim 1, comprising a plurality of transmitter antennae.

11. The calorie estimating device of claim 1, comprising a plurality of first receiver antennae, a plurality of second receiver antennae, or both.

12. The calorie estimating device of claim 1, wherein the transmitter antenna and the first receiver antenna comprise a planar transceiver antenna that is configured to transmit the UWB signals to the portion of the food item and receive at least a portion of the UWB signals reflected by the food item.

13. The calorie estimating device of claim 1, wherein the transmitter antenna, the first receiver antenna and the second receiver antenna comprise a linear polarization, an elliptical polarization or a circular polarization.

14. An open cavity system for non-destructively measuring a calorie content of a food item, the system comprising:
a calorie estimating device, comprising:
a holder substrate having at least two sides;
a transmitter antenna configured to transmit ultra-wide band (UWB) signals to at least a portion of a food item disposed on a side of the holder substrate, wherein the transmitter antenna comprises a planar antenna;

a first receiver antenna configured to receive at least a portion of UWB signals reflected by the food item, wherein the first receiver antenna comprises a planar antenna;

a second receiver antenna configured to receive at least a portion of UWB signals propagated through the food item, wherein the second receiver antenna comprises a planar antenna; and a processing unit operatively coupled to the calorie estimating device and configured to non-destructively determine a calorie content of the food items based on comparing the signals received by the first and the second receiver antennae measured both with and without the food item disposed on the holder substrate.

15. The system of claim 14, further comprising an electromagnetic source operatively coupled to the transmitter antenna and configured to generate UWB signals, wherein at least a portion of the generated UWB signals is directed to the transmitter antenna.

16. The system of claim 14, further comprising a temperature measuring device operatively coupled to the holder substrate.

17. The system of claim 14, further comprising a weighing device operatively coupled to the holder substrate.

18. A method for non-destructively measuring individual calorie contents of one or more food items, the method comprising:

irradiating an empty holder substrate with UWB signals;

acquiring at least a portion of signals reflected by the empty holder substrate;

acquiring at least a portion of signals propagated through the empty holder substrate;

irradiating the food items disposed on the holder substrate with UWB signals such that at least a portion of the UWB signals interact with the food items;

acquiring at least a portion of signals reflected by the food item;

acquiring at least a portion of signals propagated through the food item;

estimating fat contents and water contents of individual food items based on comparing the acquired reflected and transmitted signals from the empty holder substrate and the food items; and determining individual calorie contents of the food items based on the estimated fat and water contents.

19. The method of claim 18, further comprising scanning the food items with the UWB signals.

20. The method of claim 18, further comprising measuring a weight, or temperature, or both of the food item.

21. The method of claim 20, further comprising estimating the fat content and the water content of the food item based on the weight, temperature, or both of the food item.

22. The method of claim 18, wherein the UWB signals comprise a plurality of pulses.

23. The method of claim 22, wherein the plurality of pulses are successive pulses that are spaced in time.

24. The method of claim 18, wherein the UWB signals comprise a sweep frequency.

25. The method of claim 18, wherein a frequency of the UWB signals is in a range from about 100 MHz to about 20 GHz.

26. The method of claim 18, further comprising determining inverse Fourier transform of frequency domain data representing the food and water contents.

27. A kit for measuring a calorie content of a food item, comprising:

a holder substrate having at least two sides;

a transmitter antenna configured to transmit UWB signals to at least a portion of the food item disposed on a side of the holder substrate, wherein the transmitter antenna comprises a planar antenna;

a first receiver antenna configured to receive at least a portion of UWB signals reflected by the food item, wherein the first receiver antenna comprises a planar antenna;

a second receiver antenna configured to receive at least a portion of UWB signals propagated through the food item, wherein the second receiver antenna comprises a planar antenna; and wherein the kit non-destructively measures the calorie content of the food item by comparing the received signals from the first receiver and the second receiver, measured both with and without the food item disposed on the holder substrate.

* * * * *